United States Patent
Equels et al.

(10) Patent No.: US 12,312,376 B2
(45) Date of Patent: May 27, 2025

(54) THERAPEUTIC DOUBLE STRANDED RNA AND METHODS FOR PRODUCING THE SAME

(71) Applicant: AIM ImmunoTech Inc., Ocala, FL (US)

(72) Inventors: Thomas K. Equels, Ocala, FL (US); Vishwajeetsinh M. Atodaria, North Brunswick, NJ (US); Victoria G. Scott, Langhorne, PA (US); David R. Strayer, Bryn Mawr, PA (US); Peter W. Rodino, Fort Myers, FL (US)

(73) Assignee: AIM ImmunoTech Inc., Ocala, FL (US)

( * ) Notice: Subject to any disclaimer, the term of this patent is extended or adjusted under 35 U.S.C. 154(b) by 0 days.

(21) Appl. No.: 17/773,545

(22) PCT Filed: Jan. 25, 2021

(86) PCT No.: PCT/US2021/014967
§ 371 (c)(1),
(2) Date: Apr. 29, 2022

(87) PCT Pub. No.: WO2021/151099
PCT Pub. Date: Jul. 29, 2021

(65) Prior Publication Data
US 2022/0389050 A1    Dec. 8, 2022

Related U.S. Application Data

(60) Provisional application No. 63/125,950, filed on Dec. 15, 2020, provisional application No. 63/092,432, filed on Oct. 15, 2020, provisional application No. 63/016,960, filed on Apr. 28, 2020, provisional application No. 62/982,641, filed on Feb. 27, 2020, provisional application No. 62/971,199, filed on Feb. 6, 2020, provisional application No. 62/965,713, filed on Jan. 24, 2020.

(51) Int. Cl.
*C07H 21/02*    (2006.01)
*A61K 31/713*   (2006.01)

(52) U.S. Cl.
CPC .......... *C07H 21/02* (2013.01); *A61K 31/713* (2013.01)

(58) Field of Classification Search
CPC ............... A61K 31/713; A61P 31/14
USPC ............ 435/6.1, 91.1, 91.31, 455, 458; 514/44 A; 536/23.1, 24.5
See application file for complete search history.

(56) References Cited

U.S. PATENT DOCUMENTS

| | | | |
|---|---|---|---|
| 4,927,755 A | 5/1990 | De Lassauniere et al. | |
| 2011/0076296 A1* | 3/2011 | Aubin | C12N 15/117 435/325 |
| 2012/0009206 A1 | 1/2012 | Carter et al. | |
| 2014/0335112 A1* | 11/2014 | Carter | A61P 37/04 424/278.1 |

OTHER PUBLICATIONS

International Preliminary Report On Patentability (Chapter I) and Written Opinion of the International Searching Authority issued in PCT/US2021/014967; issued Jul. 26, 2022.
International Search Report issued in PCT/US2021/014967; mailed Apr. 6, 2021.
Supplementary Partial European Search Report issued by the European Patent Office on Mar. 28, 2024, which corresponds to U.S. Appl. No. 17/773,545-1111 and is related to U.S. Appl. No. 17/773,545.
Nakano Tetsuo et al: "Novel methods for nucleotide length control in double-stranded polyinosinic-polycytidylic acid production using uneven length components", Bioscience, Biotechnology, and Biochemistry, vol. 82, No. 11, Nov. 2, 2018 (Nov. 2, 2018), pp. 1889-1901.
Danilenko et al: "Development of Drugs Based on High-Polymeric Double-Stranded RNA for Antiviral and Antitumor Therapy", Biochemistry (Moscow). Supplement Series B: Biomedical Chemistry, Maik Nauka—Interperiodica, RU, vol. 13, No. 4, Oct. 1, 2019 (Oct. 1, 2019), pp. 308-323.

* cited by examiner

*Primary Examiner* — Jane J Zara
(74) *Attorney, Agent, or Firm* — Studebaker Brackett PLLC

(57) ABSTRACT

Disclosed is a method for the synthesis of a therapeutic double-stranded RNA (tdsRNA), comprising: a) synthesizing a first single-stranded RNA (first ssRNA) in a first synthesis reaction with PNPase as the only RNA polymerase; b) synthesizing a second single-stranded RNA (second ssRNA) in a second synthesis reaction with PNPase as the only RNA polymerase; and c) hybridizing the first ssRNA with the second ssRNA to form the tdsRNA; wherein step a) and step b) are performed in any order. Also disclosed is a product produced by the method.

8 Claims, No Drawings

THERAPEUTIC DOUBLE STRANDED RNA AND METHODS FOR PRODUCING THE SAME

CROSS-REFERENCE TO RELATED APPLICATIONS

This application is the U.S. National Stage of International Application No. PCT/US2021/014967 filed Jan. 25, 2021, which claims the benefit of priority to U.S. Provisional Application No. 62/965,713 filed Jan. 24, 2020, U.S. Provisional Application No. 62/971,199 filed Feb. 6, 2020, U.S. Provisional Application No. 62/982,641 filed Feb. 27, 2020, U.S. Provisional Application No. 63/016,960 filed Apr. 28, 2020, U.S. Provisional Application No. 63/092,432 filed Oct. 15, 2020, and U.S. Provisional Application No. 63/125,950 filed Dec. 15, 2020, the entire content of which is incorporated herein by reference.

BACKGROUND

This disclosure generally relates to methods of making Therapeutic Double Stranded RNA, referred to herein as "tdsRNA," and the tdsRNA made with the method.

At the end of 2019, a novel coronavirus was identified as the cause of a cluster of pneumonia cases in Wuhan, China. It rapidly spread and became a global pandemic. The disease was named novel coronavirus disease 2019 (COVID-19) and the causative agent was discovered to be a coronavirus later named SARS-CoV-2. SARS-CoV-2 is a member of the β coronavirus family. It is the seventh known coronavirus to infect humans; four of these coronaviruses (229E, NL63, OC43, and HKU1) cause slight symptoms of the common cold. The other three β coronaviruses, SARS-CoV, MERS-CoV, and SARS-CoV-2 can cause severe symptoms and even death, with fatality rates of 10%, 37%, and 5%, respectively. Over 400,000 people in the U.S. and over 2 million people worldwide have died from SARS-CoV-2 Infection. There is an urgent need for antiviral compounds that are effective against the SARS-CoV-2 virus.

BRIEF DESCRIPTION

One embodiment is directed to a method for synthesis of a therapeutic double-stranded RNA (tdsRNA), comprising the steps of: (a) synthesizing a first single-stranded RNA (first ssRNA) in a first synthesis reaction with PNPase as the only RNA polymerase; (b) synthesizing a second single-stranded RNA (second ssRNA) in a second synthesis reaction with PNPase as the only RNA polymerase; and (c) hybridizing the first ssRNA with the second ssRNA to form the tdsRNA. In the method, step (a) and step (b) can be performed in any order. In the method, the first synthesis reaction and the second synthesis reaction may comprise one or more reagents selected from the group consisting of: tris(hydroxymethyl)aminomethane buffer; $MgCl_2$; EDTA; Urea; and PNPase. In the method, the first and second synthesis may be performed in any order or simultaneously in different vessels.

In one embodiment, the first synthesis reaction may comprise inosine diphosphate (rIDP) as the only free ribonucleotide. The product produce would be $rI_n$.

In another embodiment, the second synthesis reaction may comprise cytidine diphosphate (rCDP) and uridine diphosphate (rUDP) as the only two free ribonucleotides. In any synthesis, a molar ratio of free rCDP:free rUDP in the second synthesis reaction is about (4 to 29):1, about (11 to 14):1, or about 12:1.

In another embodiment, the second synthesis reaction may comprise cytidine diphosphate (rCDP) and guanosine diphosphate (rGDP) as the only free ribonucleotides. In any synthesis a molar ratio of free rCDP:free rGDP in the second synthesis reaction is about 4 to 29:1, about 11 to 14:1, or about 12:1. In another embodiment, the second synthesis reaction may comprises cytidine diphosphate (rCDP) as the only free ribonucleotide.

In another embodiment, the first synthesis reaction comprises free Adenosine 5'-Diphosphate as the only free ribonucleotide, and the second synthesis reaction comprises free Uridine 5'-Diphosphate as the only free ribonucleotide.

In any embodiment of the disclosure, the first synthesis reaction and the second synthesis reaction are performed in the absence of adenosine triphosphate (ATP); free rNMP; free rNTP; DNA; free dNTP; free dNDP; and free dNMP.

In any of the synthesis and embodiments, the method may further comprise one or more steps selected from the group consisting of: (1) purifying said first ssRNA after the first synthesis reaction and before the hybridizing step; (2) purifying said second ssRNA after the second synthesis reaction and before the hybridizing step. Purifying may comprise purifying said first ssRNA or said second ssRNA from PNPase, and free ribonucleotides. An example of purification would be phenol extraction or ethanol precipitation.

In any embodiment, hybridizing may be performed at 62° C. to 68° C. for 5 to 30 minutes followed by 50° C. for more than 30 minutes.

In any embodiment, the method may further comprise the step of purifying the tdsRNA by filtering with 0.2 micron filter after the hybridization step.

In one embodiment, the method may comprise the following steps: (a) synthesizing a first single-stranded RNA (first ssRNA) in a first synthesis reaction with PNPase as the only RNA polymerase, and purifying said first ssRNA after the first synthesis reaction; (b) synthesizing a second single-stranded RNA (second ssRNA) in a second synthesis reaction with PNPase as the only RNA polymerase, and purifying said second ssRNA after the second synthesis reaction; and (c) hybridizing the first ssRNA with the second ssRNA. Hybridization may be, for example, incubation at 62° C. to 68° C. for 5 to 30 minutes and then incubation at 50° C. for more than 30 minutes to form the tdsRNA. In this embodiment, step (a) and step (b) may be performed in any order. In this embodiment, (1) the first synthesis reaction may comprise inosine diphosphate (rIDP) as the only free ribonucleotide; (2) the second synthesis reaction may comprise cytidine diphosphate (rCDP) and uridine diphosphate (rUDP) as the only two free ribonucleotides, and a molar ratio of (free rCDP):(free rUDP) in the second synthesis reaction is about (11 to 14):(1).

Another embodiment is directed to a tdsRNA which is produced by any of the methods of the disclosure. The tdsRNA may be at least one of the following formulas or it may be a mixture or combination of any or all of the following formulas. The formulas are as follows: $rI_n \cdot r(C_xU)_n$ (formula 1); $rI_n \cdot r(C_xG)_n$ (formula 2); $rA_n \cdot rU_n$ (formula 3); $rI_n \cdot rC_n$ (formula 4); and rugged dsRNA (formula 5).

In the formulas of this disclosure, the term "x", when present, can be at least one selected from the group consisting of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 4-29, 4-30, 14-30, 15-30, 11-14, and 30-35.

In the formulas of this disclosure, the term "n" can be a number with a value selected from the group consisting of: 40 to 50,000; 40 to 40,000; 50 to 10,000; 60 to 9000; 70 to 8000; 80 to 7000; and 380 to 450.

In any tdsRNA of this disclosure, at least 90 wt % of the tdsRNA may be larger than a size selected from the group consisting of: 40 basepairs; 50 basepairs; 60 basepairs; 70 basepairs; 80 basepairs; and 380 basepairs.

In any tdsRNA of this disclosure, at least 90 wt % of the tdsRNA is smaller than a size selected from the group consisting of: 50,000 basepairs; 10,000 basepairs; 9000 basepairs; 8000 basepairs; 7000 basepairs; and 450 basepairs.

In any tdsRNA of this disclosure, n in the formula may be from 40 to 40,000. In any tdsRNA of this disclosure, the tdsRNA may have about 4 to about 4000 helical turns of duplexed RNA strands; or the tdsRNA may have a molecular weight selected from the group consisting of: 2 kDa to 30,000 kDa, 25 kDa to 2500 kDa, and 250 kDa to 320 kDa.

As an example of one embodiment, the tdsRNA of this disclosure may comprise a mixture of $rI_n \cdot ribo(C_{11-14}U)_n$; and rugged dsRNA. For example, the tdsRNA may be $rI_n \cdot ribo(C_{12}U)_n$; and rugged dsRNA.

In any embodiment of this disclosure the rugged dsRNA may have one or more of the following characteristics: (1) a single strand comprised of $r(C_{4-29}U)_n$, $r(C_{11-14}U)_n$, or $r(C_{12}U)_n$; and (2) an opposite strand comprised of $r(I)$; wherein the single strand and the opposite strand do not base pair the position of the uracil base, and wherein the single strand and the opposite strand are partially hybridized.

In any embodiment of this disclosure the rugged dsRNA may have one or more of the following characteristics: (1) a molecular weight of about 250 kDa to 500 kDa; (2) about 400 to 800 basepairs in length; or (3) about 30 to 100 or 30-38 helical turns of duplexed RNA.

The rugged dsRNA may be a tdsRNA which is resistant to denaturation under conditions that are able to separate hybridized poly(riboinosinic acid) and poly(ribocytosinic acid) strands $(rI_n \cdot rC_n)$.

In any embodiment, the rugged dsRNA may be an isolated double-stranded ribonucleic acid (dsRNA) enzymatically active under thermal stress comprising: (A) each strand with a (A1) molecular weight of about 250 KDa to about 320 KDa, (A2) 380-450 bases, or (A3) 30 to 38 helical turns of duplex RNA; (B) a single strand comprised of poly(ribocytosinic$_{4-29}$ uracilic acid) and an opposite strand comprised of poly(riboinosinic acid), wherein the two strands do not base pair the position of the uracil base, and (C) wherein the two strands base pair the position of the cytosine base, and wherein said strands are partially hybridized.

In any embodiment, the tdsRNA may comprise 0.1-1, mol % 0.1-3 mol %, 0.1-5 mol %, 0.1-7 mol %, 0.1-9 mol %, 0.1-10 mol % or 0.1-12 mol % rugged dsRNA.

Another embodiment is directed to a therapeutic composition comprising a tdsRNA of any of this disclosure and a pharmaceutically acceptable carrier.

Another embodiment is directed to an antiviral composition comprising a tdsRNA of any of this disclosure and a pharmaceutically acceptable carrier.

Any embodiment of this disclosure may be combined with any other embodiment of this disclosure.

DETAILED DESCRIPTION

Enhanced, efficient, and cost-effective methods for manufacturing therapeutic double-stranded RNAs (tdsRNA) for therapeutic purposes are disclosed herein. The disclosed methods dispense with the use of a template nucleic acid and make the possible synthesis of tdsRNA of very high purity and therapeutic effectiveness. The tdsRNA can be administered to a subject for beneficial effects and methods of administering the tdsRNA produced are also discussed. The beneficial effects include the prevention or treatment of a virus infection such as a coronavirus infection including a SARS-CoV-2 infection.

The tdsRNA of this disclosure is beneficial to a patient regardless of the method of administration. In addition, this disclosure has made improvements to administration methods for dsRNA including tdsRNA that are superior to existing methods. Existing methods for administering therapeutic compounds are sometimes lacking in patient acceptance and compliance because these methods, such as intraparenchymal, intracerebroventricular, and intrathecal injection/infusion are invasive and cause discomfort to the patients. These limitations reduce consumer acceptance and patient compliance. In one embodiment, the tdsRNAs of this disclosure are particularly suited to solve the problem of limited acceptance and compliance because they can be administered by nasal inhalation; or a combination of nasal and oral administration; which are techniques considered more acceptable by consumers.

An added advantage of nasal administration or nasal and oral administration is that the risk and the skill level needed for this technique are much reduced compared to other techniques such as, for example, intravenous administration. This acceptance by a patient is especially important where repeated administrations are required and the patient is faced with the prospect, for example, of repeated nasal inhalation vs. repeated intravenous injection. Under times with limited professional medical assistance (war, pandemics, etc.) and acute medical need the method requires little skill level for an adult or adolescent and could be self-administered.

In some embodiments, the methods and tdsRNA of this disclosure are beneficial for treating a subject in need of treatment or prevention of a SARS-CoV-2 infection.

Definitions

"COVID-19" is a disease caused by an infection of the severe acute respiratory syndrome coronavirus 2 (SARS-CoV-2) virus. These names were standardized by the World Health Organization (WHO) and the International Committee on Taxonomy of Viruses (ICTV). Because of novelty and the rapidity of SARS-CoV-2 spread worldwide, a number of names have been used for SARS-CoV-2 including: COVID-19, COVID-19 virus, 2019-nCoV, Novel coronavirus pneumonia, and Wuhan coronavirus.

In this disclosure, it is understood that a subject with COVID-19 (the disease of COVID-19) would have an infection of SARS-CoV-2. Conversely, a subject with an infection of SARS-CoV-2 is understood to have the disease COVID-19. Also, it is understood that a subject with a disease of COVID-19 and, therefore, an infection of SARS-CoV-2, would not necessarily have any symptoms.

"r" and "ribo" have the same meaning and refer to ribonucleic acid, the nucleotide or nucleoside that are the building block of ribonucleic acid.

RNA consists of a chain of linked units called nucleotides. Unless otherwise specified, the nucleotides and bases expressed refers to the ribo form of the nucleotide or base (i.e., ribonucleotide with one or more phosphate groups). Therefore "A" refers to rA or adenine, "U" refers to rU or uracil, "C" refers to rC or cytosine, "G" refers to rG or guanine, "I" refers to rI or inosine, "rN" refers to rA, rU, rC, rG or rI. Each of these (i.e., A, U, C, G, I) may have one or more phosphate groups as discussed above.

"n" is an integer and refers to the length of the ssRNA or dsRNA in bases or basepairs.

A free nucleotide is a nucleotide that has not been incorporated into an RNA chain. The free nucleotide may be incorporated into an RNA chain by an enzyme such as an RNA polymerase, and, after such incorporation, the nucleotide is no longer considered a free nucleotide. Examples of free nucleotides would include free rA, free rU, free rC, free rG, free rI, free rN.

An RNA (RNA molecule) may have a ratio of nucleotides or bases. For example, $r(C_{12}U)_n$ denotes a single RNA strand which has, on average 12 C bases or nucleotides for every U base or nucleotide. As another example, $r(C_{11-14}U)_n$ denotes a single RNA strand that has, on average 11 to 14 C bases or nucleotides for every U base or nucleotide.

Formulas: As an example, the formula "$rI_n \cdot r(C_{12}U)_n$" can be expressed as $riboI_n \cdot ribo(C_{12}U)_n$, $rI_n \cdot ribo(C_{12}U)_n$, or $riboI_n \cdot r(C_{12}U)_n$, refers to a double-stranded RNA with two strands. One strand ($rI_n$) is poly ribo-inosine of n bases in length. The other strand is ssRNA of random sequence of C and U bases but which has a defined ratio of C and U bases. The random sequence ssRNA is n bases in length, and a ratio of C bases to U bases in the random sequence ssRNA is about 12 (i.e., mean 12 C to 1 U).

The "•" symbol indicates that one strand of the dsRNA is hybridized (hydrogen-bonded) or mostly hybridized to the second strand of the same dsRNA. Therefore, $rI_n \cdot r(C_{12}U)_n$ is double-stranded RNA comprising two ssRNA. One ssRNA is poly(I) and the other ssRNA is poly($C_{12}U$). It should be noted that while we referred to the two strands being hybridized, not 100% of the bases form base pairing as there are some bases that are mismatches. Also, because rU does not form base pairing with rI as well as rC form base paring with rI, rU provides a focus of hydrodynamic instability in $rI_n \cdot r(C_{12}U)_n$ at the locations of the U bases."

As another example, the formula "$rI_n \cdot r(C_{11-14}U)_n$" refers to the same dsRNA in the previous paragraph except that a ratio of C bases to U bases one strand is about 11 to about 14. That is, the ratio can be 11, 12, 13 or 14 or any value including non-integer values, between 11 and 14. For example, when half of the strands are $r(C_{12}U)_n$ and half of the strands are $r(C_{13}U)_n$, the formula would be $r(C_{12.5}U)_n$.

As discussed earlier, the term "r" and "ribo" has the same meaning in the formulas of the disclosure. Thus, rI, riboI, r(I) and ribo(I) refer to the same chemical which is the ribose form of inosine. Similarly, rC, riboC, r(C) and ribo(C) all refer to cytidine in the ribose form which is a building block of RNA. rU, riboU, r(U) and ribo(U) all refer to Uracil in the ribose form which is a building block of RNA.

In this disclosure, PNPase refers to Polynucleotide Phosphorylase (PNPase) and not to another, otherwise unrelated enzyme, Purine nucleoside phosphorylase.

A nucleotide triphosphate (rNTP), as used herein, refers to a molecule including a nucleobase linked to a ribose (i.e. nucleoside) and three phosphates (i.e. nucleotide). A nucleotide diphosphate (rNDP) refers to the same molecule, but which has two phosphate moieties. A nucleotide monophosphate (rNMP) refers to the same molecule, but which has one phosphate moiety. The nucleotide monophosphate, diphosphate, and triphosphate are sometimes referred to herein as rNMP, rNDP, and rNTP, respectively. The N in rNMP, rNDP and rNTP refer to any nucleotide, including naturally occurring nucleotides, synthetic nucleotides, and modified nucleotides. Thus the terms rNMP, rNDP and rNTP refer to nucleotide monophosphate, nucleotide diphosphate and nucleotide triphosphate, respectively. These terms (rNMP, rNDP and rNTP) also refer to any nucleotide having any naturally occurring, synthetic, or modified nucleotide therein. The methods and products of this disclosure are all RNAs and thus unless otherwise noted all references to nucleic acids are referring to the ribose form. That is, unless otherwise noted, NMP, NDP, NTP, IMP, IDP, ITP, CMP, CDP, CTP, UMP, UDP, UTP refers to rNMP, rNDP, rNTP, rIMP, rIDP, rITP, rCMP, rCDP, rCTP, rUMP, rUDP, rUTP respectively.

In this disclosure, inosine is also considered a possible rNMP, rNDP or rNTP. Inosine is a nucleoside that is formed when hypoxanthine is attached to a ribose ring (also known as a ribofuranose) via a β-N9-glycosidic bond.

Nucleotide monophosphates include at least adenosine monophosphate (AMP or rAMP), guanosine monophosphate (GMP or rGMP), cytidine monophosphate (CMP or rCMP), uridine monophosphate (UMP or rUMP), and inosine monophosphate (IMP rIMP). Nucleotide diphosphates include at least adenosine diphosphate (ADP or rADP), guanosine diphosphate (GDP or rGDP), cytidine diphosphate (CDP or rCDP), uridine diphosphate (UDP or rUDP), and inosine diphosphate (IDP or rIDP).

Nucleotide triphosphates include at least adenosine triphosphate (ATP or rATP), guanosine triphosphate (GTP or rGTP), cytidine triphosphate (CTP or rCTP), uridine triphosphate (UTP or rUTP), and inosine triphosphate (ITP or rITP).

In a preferred embodiment, the tdsRNA produce by the methods on this disclosure may comprise no detectable ssRNA (more than 0% to less than 0.1%). In a preferred embodiment, the tdsRNA may comprises between 0.1% to 4% ssRNA, between 0.5% to 3% ssRNA, and preferably between 1.5% to 2.5% ssRNA. The ssRNA may be present at the ends of the tdsRNA—in other words, the ends of the tdsRNA may be single-stranded (also called "sticky ends"). The single-stranded region may be a 5' overhang or a 3' overhang. A single-stranded region may also be internal such as if the bases are not paired due to temperature or salt conditions or if one strand is longer than the complementary strand causing a loop structure where one strand of the double-stranded RNA comprises an internal loop of single-stranded RNA.

While this disclosure refers to dsRNA and tdsRNA, it is not required that the tdsRNA comprising only two ssRNA in duplex. For example, tdsRNA may comprise one strand of 300 bases and (1) two opposite strands of 150 bases each, or three opposite strands of 100 bases each.

The dsRNA (tdsRNA) and ssRNA of this disclosure are homopolymers or heteropolymers of limited base composition and not mRNA and are distinct from mRNA in structure. For example, the ssRNA and dsRNA are preferably missing one or all of the following: (1) 5' cap addition, (2) polyadenylation, (3) start codon, (4) stop codon, heterogeneous protein-coding sequences, and (5) spice signals.

As used herein, the term "substantially free" is used operationally, in the context of analytical testing of the material. Preferably, purified material is substantially free of one or more impurities. In a preferred embodiment, the tdsRNA of this disclosure is substantially free (e.g., more than 0% to less than 0.1%) or completely free (0%) of dI/dI dsRNA or dCdU/dCdU dsRNA. In other words, the tdsRNA is substantially free or completely free (0%) of homodimers of polymer 1 or homodimers of polymer 2. Substantially free in this context would be considered to be more than 0% but less than 1%, less than 0.5%, less than 0.2%, less than 0.1%, or less than 0.01% of a contaminant such as (1) dl/dl (polymer 1/polymer 1) tdsRNA, dCdU)/(dCdU (polymer 2/polymer 2) dsRNA.

COVID-19 and SARS-CoV-2

The present disclosure provides double-stranded RNA (referred to herein as "therapeutic double-stranded RNA" or "tdsRNA" and described in more detail below) and methods for using these dsRNAs (tdsRNA) in the treatment (e.g., therapeutic and/or prophylactic) of a SARS-CoV-2 infection.

Thus, methods for treating SARS-CoV-2 infections and preventing spread of the virus and further infection are objectives of the present disclosure.

There is an urgent need for treatment of subjects who have been exposed to SARS-CoV-2 but have not developed symptoms of SARS-CoV-2 infection (e.g., fever, dry cough and difficulty breathing). The period between exposure and symptoms may be one to five days, one week, 10 days, two weeks or more. Timely treatment may allow a subject to reduce the time of viral infection and, if treatment was applied early enough, escape symptoms altogether. For example, if a patient was determined to have contact with SARS-CoV-2, the healthcare workers can be treated with the methods and compositions (tdsRNA) of this disclosure to reduce the chances of developing a SARS-CoV-2 infection (COVID-19 disease) or to reduce or eliminate the symptoms thereof.

Viral infection may be diagnosed in subjects to identify those who are affected and need treatment. While a large population can be rapidly screened for those having a high body temperature, such screening is neither specific nor sensitive. Better detection of infection for diagnosis is preferred: (i) PCR or serologic assay for the presence of nucleic acids or proteins, respectively, specific for SARS-CoV-2 in a specimen obtained from a subject suspected of being infected (e.g., respiratory material such as nasopharyngeal or oropharyngeal swab, sputum, endotracheal aspirate, and bronchoalveolar lavage, serum or whole blood, and urine), or (ii) by the subject's symptoms such as high fever, dry cough, and difficulty breathing), leading to pneumonia and severe acute respiratory syndrome. Detection of endemic human coronaviruses (e.g., HCoV-229E, HCoV-NL63, HCoV-HKU1 and HCoV-OC43) is not required, but they should be excluded from diagnosis by using assay reagents specific for SARS-CoV-2. After sequencing a sufficient number of SARS-CoV-2 isolates and developing specific assay reagents (e.g., primers, probes, antibodies) therefrom, confirmatory sequencing should not be necessary.

There is also an urgent need for preventing infection from SARS-CoV-2 for example, by administering an agent with a prophylactic effect on a subject. That is, after treatment, the subject would be less susceptible to infection with SARS-CoV-2.

The various treatments would be especially useful and effective for subjects at a heightened risk of contracting the disease. They may be those who are in close proximity (e.g., presence within about two meters or in the same enclosed room) to an infected individual. For example, prophylactic treatment would be useful for healthcare workers, public safety workers, police, airport workers, teachers, students, transportation workers and people traveling into or out of an infected region (i.e., between an infected region and an uninfected region). For example, the first diagnosed case of Wuhan coronavirus infection in the US has exposed over 40 individuals to the virus before he was hospitalized. Currently, there are thousands of persons in quarantine globally because of possible exposure to the virus.

tdsRNA, Formulations Thereof and Medicaments Thereof

The double-stranded RNAs described in this disclosure are therapeutic double-stranded "tdsRNA" which has a number of benefits when administered either by itself or with other medicaments and pharmaceuticals to a subject. In one embodiment, the "tdsRNA" which can serve in a therapeutic capacity as well as in a preventative capacity against SARS-CoV-2 infection. All of the tdsRNAs of this disclosure are designed to reduce the SARS-CoV-2 viral load and/or prevent or at least reduce the risk of SARS-CoV-2 infection of a susceptible individual. In other embodiments, the tdsRNA has anti-cancer effects, antiviral effects, or an adjuvant effect when administered with a vaccine.

Methods (Processes) for Making tdsRNA

One embodiment is directed to a method for the synthesis of a therapeutic double-stranded RNA (tdsRNA). The method comprises the steps of a) synthesizing a first single-stranded RNA (first ssRNA) in a first synthesis reaction with PNPase as the only RNA polymerase, b) synthesizing a second single-stranded RNA (second ssRNA) in a second synthesis reaction with PNPase as the only RNA polymerase, and c) hybridizing the first ssRNA with the second ssRNA to form the tdsRNA, wherein step a) and step b) are performed in any order. Similarly, in any method for the synthesis of both strands of a tdsRNA, the order of strand synthesis may be in any order. "In any order" as used herein means that one strand may be synthesized before a second strand or vice versa. Further, both strands may be synthesized at the same time in different synthesis reactions in different vessels.

In the method above, or in any embodiment of the disclosure, the first synthesis reaction and the second synthesis reaction comprise one or more reagents selected from the group consisting of: tris(hydroxymethyl)aminomethane buffer, $MgCl_2$, EDTA, Urea and PNPase.

In any embodiment of the disclosure, the first synthesis reaction may comprise inosine diphosphate (rIDP) as the only free ribonucleotide. One nonlimiting example of a product that can be made with this embodiment is $rI_n \cdot r(N)_n$ wherein $r(N)_n$ represents a ssRNA or analog thereof of any sequence.

In any embodiment of the disclosure, the second synthesis reaction may comprise cytidine diphosphate (rCDP) and uridine diphosphate (rUDP) as the only free ribonucleotides. In one embodiment, the molar ratio of free rCDP/free rUDP in the second synthesis reaction may be any positive number but is preferably about 4 to 29, about 11 to 14, or about 12. Nonlimiting examples of products that can be made with this embodiment include $rI_n \cdot r(C_xU)_n$, $rI_n \cdot r(C_4\text{-}29U)_n$, $rI_n \cdot r(C_{11\text{-}14}U)_n$, $rI_n \cdot r(C_{12}U)_n$, where x may be any non-zero number.

In any embodiment of the disclosure, the second synthesis reaction may comprise cytidine diphosphate (rCDP) and guanosine diphosphate (rGDP) as the only free ribonucleotides. In one embodiment, a molar ratio of free rCDP/free rGDP in the second synthesis reaction is about 4 to 29, about 11 to 14, or about 12. Nonlimiting examples of products that can be made with this embodiment include $rI_n \cdot r(G_xU)_n$, $rI_n \cdot r(G_{4\text{-}29}U)_n$, $rI_n \cdot r(G_{11\text{-}14}U)_n$, $rI_n \cdot r(G_{12}U)_n$, where x may be any positive non zero number.

In any embodiment of the disclosure, the second synthesis reaction comprises cytidine diphosphate (rCDP) as the only free ribonucleotide. A nonlimiting example of products that can be made with this embodiment includes $rI_n \cdot rC_n$.

In any embodiment of the disclosure, the first synthesis reaction may comprise free Adenosine 5'-Diphosphate as the only free ribonucleotide, and the second synthesis reaction may comprise free Uridine 5'-Diphosphate as the only free ribonucleotide. A nonliming example of products that can be made with this embodiment includes $rA_n \cdot rU_n$.

In one embodiment, the first synthesis reaction and the second synthesis reaction are performed in the absence of a number of reagents including adenosine triphosphate (ATP), rNMP (ribonucleotide mono phosphates), rNTP (ribonucleotide triphosphates), DNA (deoxynucleic acids), dNTP (deoxynucleotide triphosphates), dNDP (deoxynucleotide diphosphates), dNMP (deoxynucleotide monophosphates).

In any embodiment of this disclosure, the methods may include one or more optional steps as follows: (1) purifying said first ssRNA after the first synthesis reaction and before the hybridizing step, (2) purifying said second ssRNA after the second synthesis reaction and before the hybridizing step. Purifying refers to purifying the first ssRNA or the second ssRNA from proteins such as PNPase and/or purifying the first ssRNA from the other components of the reaction including, for example, ribonucleotide diphosphates.

In any embodiment of this disclosure, the hybridizing step may be performed by bringing a mixture of equal molar amounts of two ssRNA and incubating the two ssRNA in an aqueous solution at 62° C. to 68° C. for 5 to 30 minutes and then 50° C. for more than 30 minutes. The sum of the concentrations of the first ssRNA and the second ssRNA may be, for example, 7.9 mM. The hybridization solution may be, for example, sodium phosphate buffer (150 mM NaCl, 1 mM MgCl$_2$, 8 mM Na$_2$HPO$_4$, 1.6 mM NaH$_2$PO$_4$). Unless otherwise specified, this hybridization step can be used to form a dsRNA, which can be a tdsRNA, from two ssRNAs for any embodiment of this disclosure.

In any embodiment of this disclosure, the tdsRNA, dsRNA, or ssRNA may be purified by filtering with a 0.2-micron filter. For example, in the methods of the disclosure, the method may comprise an optional step which is to purify the RNA by filtering through a 0.2-micron filter after the hybridization step.

The methods of this disclosure produce tdsRNA that is effective against a broad range of viruses such as the viruses listed in this disclosure. These viruses include, at least the coronaviruses such as for example, SARS-CoV-2 and strains and variants thereof.

tdsRNA

The double-stranded RNAs described in this disclosure are therapeutic double-stranded RNA, abbreviated as "tdsRNA." tdsRNA includes, at least, rintatolimod (which is at least a tdsRNA of the formula $rI_n \cdot r(C_{12}U)_n$, described below as formula 1). tdsRNA may be stored or administered in a pharmaceutically acceptable solution such as Phosphate Buffered Saline (PBS).

The tdsRNA may be a tdsRNA produced by any of the methods of this disclosure—referred to herein as the "tdsRNA Product" or "tdsRNA"—the two terms have the same meaning. tdsRNA can be represented by one or more of the formulas below in any combination:

 (formula 1)

 (formula 2)

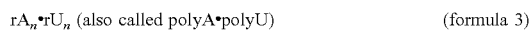 (formula 3)

 (formula 4)

rugged dsRNA (formula 5)

Each will be discussed further below.

The tdsRNA may be represented by one or more of the formulas as follows:

 (formula 1)

 (formula 2)

x may be at least one selected from the group consisting of: 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 4-29 (4 to 29), 4-30 (4 to 30), 4-35 (4 to 35), 11-14 (11 to 14), 30-35 (30 to 35). Of these, x=12, and x=11-14 (x may be any value between 11 to 14) are especially preferred. "x" is a ratio between two types of bases (e.g., C and U, or C and G) and therefore x can have a non-integer value such as 12.5, 4.5, 9.6, 29.1 and the like. Since n represents the length for both strands, both strands of ssRNA are the same length which gives rise to a dsRNA with no significant single-stranded regions in the middle or at the end of the double-stranded structure.

In these formulas 1 to 5, and in other formulas, where there is no subscript next to a base, the default value is "1." For example, in the formula $rI_n \cdot r(C_{12}U)_n$, there is no subscript following "U," it is understood that $rI_n \cdot r(C_{12}U)_n$ is the same as $rI_n \cdot r(C_{12}U_1)_n$ and the formula is meant to convey that for the strand denoted as $r(C_{12}U_1)_n$, there are 12 rC base for every rU base. Thus, x is also a ratio of the bases of one strand of the tdsRNA. The length of the tdsRNA strand is denoted as a lowercase "n" (e.g., $rI_n \cdot r(C_{12}U)_n$). The subscript n is also the length of each individual single stranded nucleic acid. Since tdsRNA is double stranded, n is also the length of the double stranded nucleic acid—i.e., the length of the tdsRNA. For example, $rI_n \cdot r(C_{12}U)_n$ in intended to indicate, inter alia, a double stranded RNA with each strand with a length of n.

In another embodiment, the tdsRNA may have a formula as follows:

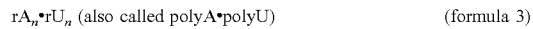 (formula 3)

 (formula 4)

In another embodiment, the tdsRNA may be a rugged dsRNA (formula 5).

In one embodiment, tdsRNA is one or more at least one selected from the group consisting of formula 1, formula 2, formula 3, formula 4, and formula 5. In another embodiment, tdsRNA comprises formula 1 and formula 2 only. In one preferred embodiment, tdsRNA comprises formula 1 only. In another embodiment, tdsRNA comprises formula 1 and formula 5 (rugged dsRNA) only.

In another embodiment, at least 70%, at least 80%, or at least 90% of the tdsRNA may have a molecular weight of between 400,000 Daltons to 2,500,000 Daltons. Where the term percent ("%") is used, the percent may be weight percent or molar percent.

In another embodiment, the tdsRNA comprises a first ssRNA and a second ssRNA and each of these first ssRNA or second ssRNA may contain one or more strand breaks.

In another embodiment, the tdsRNA may comprise at least one selected from the group consisting of: a 3' overhang end, a 5' overhang end, a blunt end, an internal ssRNA sequence, one or more strand breaks in a first ssRNA, and one or more strand breaks in a second ssRNA.

In another embodiment, the tdsRNA is a linear molecule—that is a molecule that is not branched or that does not contain any loop structure. In different embodiments, at least 60%, at least 70%, at least 80%, at least 90%, at least 95% or 100% of the tdsRNA is a linear molecule.

In another embodiment, the tdsRNA has the property that greater than about 90%, greater than 95%, greater than 98%, greater than 99%, or 100% of the bases of the RNA are in a double-stranded configuration.

In any embodiment, the tdsRNA may be in a therapeutic composition comprising, for example, a tdsRNA, and a pharmaceutically acceptable excipient.

One embodiment of tdsRNA is directed to rintatolimod, which is a tdsRNA of the formula $rI_n \cdot r(C_{12}U)_n$.

In a preferred embodiment, the tdsRNA are of the general formula $rI_n \cdot r(C_{11-14}, U)_n$ and are described in U.S. Pat. Nos. 4,024,222 and 4,130,641 (which are incorporated by reference herein) or synthesized according to this disclosure.

In the case where the tdsRNA is $rA_n \cdot rU_n$, the tdsRNA may be matched (i.e., not in mismatched form).

tdsRNA has undergone extensive clinical and preclinical testing. It has been generally well-tolerated in clinical trials enrolling over 1,200 patients with over 100,000 doses administered and there have been no drug-related deaths. Two placebo-controlled, randomized studies show no increase in serious adverse events compared to placebo. Favorable safety profiles have been seen for intraperitoneal, intravenous, and intranasal routes of administration of tdsRNA.

Length of tdsRNA

The length of the tdsRNA, may be represented by bases for one strand of the tdsRNA or in basepairs for both strands for the tdsRNA. It is understood that in some embodiments that not all of the bases (e.g., U and I) are in basepaired configuration. For example, rU bases do not pair as well as rC bases to inosine.

The length of the tdsRNA may be measured by (1) bases or basepairs, (2) molecular weight which is the weight of the double stranded tdsRNA (e.g., Daltons) or (3) turns of the double stranded RNA. These measurements can be easily interconverted. For example, it is generally accepted that there are about 629 Daltons per base pair.

"n" represents length in units of basepair or basepairs (abbreviated as bp regardless of whether it is singular or plural) for double stranded nucleic acid. "n" can also represent bases for single stranded RNA. Because "bp" represents singular or plural, it is the same as "bps" which is another representation of basepairs.

The tdsRNA can have the following values for its length "n" (in bases for single strand or basepairs for double strands): 4-5000, 10-50, 10-500, 10-40,000, 40-40,000, 40-50,000, 40-500, 50-500, 100-500, 380-450, 400-430, 400-800 or a combination thereof. Expressed in molecular weight, the tdsRNA may have the following values: 30 kDa to 300 kDa, 250 kDa to 320 kDa, 270 kDa to 300 kDa or a combination thereof. Expressed in helical turns, the tdsRNA may have 4.7 to 46.7 helical turns of duplexed RNA, 30 to 38 helical turns of duplexed RNA, 32 to 36 helical turns of duplexed RNA or a combination thereof.

The length may be an average basepair, average molecular weight, or an average helical turns of duplexed RNA and can take on integer or fractional values.

tdsRNA Preparation

One embodiment is directed to a method for the synthesis of a therapeutic double-stranded RNA (tdsRNA). The method comprises the steps of a) synthesizing a first single-stranded RNA (first ssRNA) in a first synthesis reaction with PNPase as the only RNA polymerase, b) synthesizing a second single-stranded RNA (second ssRNA) in a second synthesis reaction with PNPase as the only RNA polymerase, and c) hybridizing the first ssRNA with the second ssRNA to form the tdsRNA, wherein step a) and step b) are performed in any order. Similarly, in any method for the synthesis of both strands of a tdsRNA, the order of strand synthesis may be in any order. "In any order" as used herein means that one strand may be synthesized before a second strand or vice versa. Further, both strands may be synthesized at the same time in different synthesis reactions in different vessels.

In the method above, or in any embodiment of the disclosure, the first synthesis reaction and the second synthesis reaction comprise one or more reagents selected from the group consisting of: tris(hydroxymethyl)aminomethane buffer, $MgCl_2$, EDTA, Urea and PNPase.

In any embodiment of the disclosure, the first synthesis reaction may comprise inosine diphosphate (rIDP) as the only free ribonucleotide. One nonlimiting example of a product that can be made with this embodiment is $rI_n \cdot r(N)_n$ wherein $r(N)_n$ represents a ssRNA or analog thereof of any sequence.

In any embodiment of the disclosure, the second synthesis reaction may comprise cytidine diphosphate (rCDP) and uridine diphosphate (rUDP) as the only free ribonucleotides. In one embodiment, the molar ratio of free rCDP/free rUDP in the second synthesis reaction may be any positive number but is preferably about 4 to 29, about 11 to 14, or about 12. Nonlimiting examples of products that can be made with this embodiment include $rI_n \cdot r(C_xU)_n$, $rI_n \cdot r(C_{4-29}U)_n$, $rI_n \cdot r(C_{11-14}U)_n$, $rI_n \cdot r(C_{12}U)_n$, where x may be any non-zero number.

In any embodiment of the disclosure, the second synthesis reaction may comprise cytidine diphosphate (rCDP) and guanosine diphosphate (rGDP) as the only free ribonucleotides. In one embodiment, a molar ratio of free rCDP/free rGDP in the second synthesis reaction is about 4 to 29, about 11 to 14, or about 12. Nonlimiting examples of products that can be made with this embodiment include $rI_n \cdot r(G_xU)_n$, $rI_n \cdot r(G_{4-29}U)_n$, $rI_n r(G_{11-14}U)_n$, $rI_n \cdot r(G_{12}U)_n$, where x may be any positive nonzero number.

In any embodiment of the disclosure, the second synthesis reaction comprises cytidine diphosphate (rCDP) as the only free ribonucleotide. A nonlimiting example of products that can be made with this embodiment includes $rI_n \cdot rC_n$.

In any embodiment of the disclosure, the first synthesis reaction may comprise free Adenosine 5'-Diphosphate as the only free ribonucleotide, and the second synthesis reaction may comprise free Uridine 5'-Diphosphate as the only free ribonucleotide. A nonlimiting example of products that can be made with this embodiment include rAn•rUn.

In any embodiment of the disclosure, synthesis may begin by the addition of PNPase. PNPase may be added for example, in the range of 500-700 Units per Liter of reaction.

In one embodiment, the first synthesis reaction and the second synthesis reaction are performed in the absence of a number of reagents including adenosine triphosphate (ATP), rNMP (ribonucleotide mono phosphates), rNTP (ribonucleotide triphosphates), DNA (deoxynucleic acids), dNTP (deoxynucleotide triphosphates), dNDP (deoxynucleotide diphosphates), dNMP (deoxynucleotide monophosphates).

In any embodiment of this disclosure, the methods may include one or more optional steps as follows: (1) purifying said first ssRNA after the first synthesis reaction and before the hybridizing step, (2) purifying said second ssRNA after the second synthesis reaction and before the hybridizing step. Purifying refers to purifying the first ssRNA or the second ssRNA from proteins such as PNPase and/or purifying the first ssRNA from the other components of the reaction including, for example, ribonucleotide diphosphates.

In any embodiment of this disclosure, the hybridizing step may be performed by bringing a mixture of equal molar amounts of two ssRNA and incubating the two ssRNA in an aqueous solution at 62° C. to 68° C. for 5 to 30 minutes and then 50° C. for more than 30 minutes. The sum of the concentrations of the first ssRNA and the second ssRNA may be, for example, 7.9 mM. The hybridization solution may be, for example, sodium phosphate buffer (150 mM NaCl, 1 mM $MgCl_2$, 8 mM $Na_2HPO_4$, 1.6 mM $NaH_2PO_4$). Unless otherwise specified, this hybridization step can be used to form a dsRNA, which can be a tdsRNA, from two ssRNAs for any embodiment of this disclosure.

In any embodiment of this disclosure, the tdsRNA, dsRNA, or ssRNA may be purified by filtering with a 0.2-micron filter. For example, in the methods of the disclosure, the method may comprise an optional step which is to purify the RNA by filtering through a 0.2-micron filter after the hybridization step.

Rugged dsRNA Preparation

In one embodiment, the starting material for making Rugged dsRNA may be dsRNA prepared in vitro using the methods of this disclosure. Also, the dsRNA described in U.S. Pat. Nos. 4,024,222, 4,130,641, and 5,258,369 (which are incorporated by reference herein) are suitable as starting materials after selection for rugged dsRNA. As another example, the tdsRNA as synthesized according to the current disclosure are suitable as starting materials after selection for rugged dsRNA.

After procuring starting material, Rugged dsRNA may be isolated by at least subjecting the partially hybridized strands of a population of dsRNA to conditions that denature most dsRNA (more than 50 wt % or mol %, more than 60 wt % or mol %, more than 70 wt % or mol %, more than 80 wt % or mol %, more than 90 wt % or mol %, more than 95 wt % or mol %, or more than 98 wt % or mol %) in the population, and then selection negatively or positively (or both) for dsRNA that remain partially hybridized. The denaturing conditions to unfold at least partially hybridized strands of dsRNA may comprise an appropriate choice of buffer salts, pH, solvent, temperature, or any combination thereof. Conditions may be empirically determined by observation of the unfolding or melting of the duplex strands of ribonucleic acid. The yield of rugged dsRNA may be improved by partial hydrolysis of longer strands of ribonucleic acid, then selection of (partially) hybridized stands of appropriate size and resistance to denaturation.

The purity of rugged dsRNA, which functions as tdsRNA, may thus be increased from less than about 1-12 mol % (e.g., less than 1%, less than 2%, less than 3%, less than 4%, less than 5%, less than 6%, less than 7%, less than 8%, less than 9%, less than 10%, less than 11%, less than 12%) rugged dsRNA relative to all RNA in the population after synthesis (e.g., using the method of this disclosure) to a higher purity. In each case the starting material may have more than 0.1 mol % or wt % rugged dsRNA, 0.5 mol % or wt % rugged dsRNA, or 1 mol % or wt % rugged dsRNA. A higher purity of rugged dsRNA may be more than 20 wt % or mol %, more than 30 wt % or mol %, more than 40 wt % or mol %, more than 50 wt % or mol %, more than 60 wt % or mol %, more than 70 wt % or mol %, more than 80 wt % or mol %, more than 90 wt % or mol %, and more than 98 wt % or mol %. All wt % or mol % is relative to all RNA present in the same composition.

Another method of isolating Rugged dsRNA is to employ chromatography. Under analytical or preparative high-performance liquid chromatography, Rugged dsRNA can be isolated from a preparation (e.g., the starting material as described above) to produce poly(I):poly($C_{12}U)_n$ (e.g., poly (I):poly($C_{11-14}U)_n$) as a substantially purified and pharmaceutically active molecule with an HPLC peak of about 4.5 to 6.5 minutes, preferably between 4.5 and 6 minutes and most preferably 5 minutes.

Stabilizing Polymers

In any of the described embodiments, the tdsRNA may be complexed with a stabilizing polymer such as: polylysine, polylysine plus carboxymethylcellulose (lysine carboxy methyl cellulose), polyarginine, polyarginine plus carboxymethylcellulose, or a combination thereof. Some of these stabilizing polymers are described, for example, in U.S. Pat. No. 7,439,349.

Modified Backbone

The tdsRNA may comprise one or more alterations in the backbone of the nucleic acid. For example, configured tdsRNA may be made by modifying the ribosyl backbone of poly (riboinosinic acid) $r(I_n)$, for example, by including 2'-O-methylribosyl residues. Specifically configured dsRNA may also be modified at the molecule's ends to add a hinge(s) to prevent slippage of the base pairs, thereby conferring specific bioactivity in solvents or aqueous environments that exist in human biological fluids.

Length

Where "n" is the length of the tdsRNA (in basepairs) and n is an integer having a value of from 40 to 50,000, 40 to 40,000, 10 to 40,000, 10 to 500, 10 to 50 or 40 to 500.

Formulation

Formulations for administration (i.e., pharmaceutical compositions) may include a pharmaceutically acceptable carrier with the tdsRNA.

Pharmaceutically acceptable carriers may be, for example, aqueous solutions, syrups, elixirs, powders, granules, tablets, and capsules which typically contain conventional excipients such as binding agents, fillers, lubricants, disintegrants, wetting agents, suspending agents, emulsifying agents, preservatives, buffer salts, flavoring, coloring, and/or sweetening agents. The preferred formulation may vary with the age, condition, gender, or health status of the subject, the nature of the disease or other pathological condition, including the number and severity of symptoms, and the chosen active ingredient.

The tdsRNA in solid form may be dissolved using known diluents for administration such as, for example, physiological phosphate-buffered saline, and then infused intravenously. The tdsRNA may be a combination or any subset of dsRNA described above. It is understood that in one embodiment, tdsRNA may comprise a combination of all of the examples of tdsRNA described above or any subset of the above examples. With respect to the subsets, the specific exclusion of one or more specific embodiment of tdsRNA is also envisioned. As non-limiting examples, tdsRNA may comprise any one or more of the following: (1) all of the examples of tdsRNA as described above, (2) all of the examples of tdsRNA described above but without $rI_n \cdot r(C_{11-14}U)_n$, (3) Rugged dsRNA, (4) $rI_n \cdot r(C_{12}U)_n$, (5) tdsRNA as described above but without $rI_n \cdot r(C_{11-14}U)_n$ and without Rugged dsRNA; (6) a combination of $rI_n \cdot r(C_{12}U)_n$ and rugged dsRNA, and (7) a combination of $rI_n \cdot r(C_{11-14}U)_n$ and rugged dsRNA.

Nasal Compositions

In one embodiment, a composition for enhancing intranasal delivery includes a combination of tdsRNA and active compounds prepared for nasal delivery. The combination of tdsRNA and active compounds may be applied in a subsequent manner or a simultaneous manner. In a preferred embodiment, the mixture will be in the form of an aqueous solution. In other embodiments, the mixture will be a powder or a dried, powdered, or lyophilized form of the mixture. In some embodiments, these forms will be rehydrated before delivery.

In one embodiment, the present disclosure relates to formulations for nasal delivery of tdsRNA. In one embodiment, tdsRNA is the sole active compound and may be free of any other active compounds. In another embodiment, the tdsRNA may be co-administered with one or more additional active compounds.

Each of the agents and chemicals described herein, including any combinations thereof, may be added to a tdsRNA for administration, including nasal administration, to a subject. Pharmaceutically acceptable agents and chemicals are preferred. These compounds may comprise traditional pharmaceutical carriers such as water and or phosphate buffered saline or saline. These compounds may additionally comprise, for example, one or more of the following: Antiviral compounds such as monoclonal antibodies, Oseltamivir, Zanamivir or Peramivir. Carrier or vehicle such as sugars, cellulose, oils, isotonic saline, antioxidants, or ascorbic acid. Absorption-promoting agents such as deacyl methyl sulfoxide, azone, or sodium lauryl sulfate. Delivery-enhancing agents such as DMSO. Mucolytic or mucus clearing agents such as proteases (e.g., pronase, papain) and detergents (e.g., Triton X-100, Tween 20). Ciliostatic agents such as 2-alkyl-4-hydroxyquinolines or rhamnolipid (also known as a hemolysin). Penetration-Promoting agent such as sodium salicylate and salicylic acid derivatives (acetyl salicylate, choline salicylate, salicylamide, etc.), amino acids and salts thereof (e.g., monoaminocarboxlic acids such as glycine, alanine, phenylalanine, proline, hydroxyproline). Vasodilator or vasoconstrictor agents such as potassium channel openers, ACE inhibitors, angiotensin-II receptor antagonists, alpha-adrenergic and imidazole receptor antagonists, beta-1-adrenergic agonists, phosphodiesterase inhibitors, eicosanoids and NO donors. RNase inhibitory agents such as SUPERase, In RNase Inhibitor, RNaseOUT, RNAsecure, and RNase Inhibitor. Selective transport-enhancing agents such as glycosides, sugar-containing molecules, and binding agents such as lectin binding agents, and stabilizers. Specific "bioadhesive" ligands, including various plant and bacterial lectins, which bind to cell surface sugar moieties by receptor-mediated interactions can be employed as carriers or conjugated transport mediators for enhancing mucosal, e.g., nasal delivery of biologically active agents within the disclosure.

Mucosal delivery-enhancing agents such as mixed micelles, enamines, nitric oxide donors (e.g., S-nitroso-N-acetyl-DL-penicillamine, NOR1, NOR4—which are preferably co-administered with an nitric oxide scavenger such as carboxy-PITO or diclofenac sodium), sodium salicylate, glycerol esters of acetoacetic acid (e.g., glyceryl-1,3-diacetoacetate or 1,2-isopropylideneglycerine-3-acetoacetate).

Medicament

In another embodiment, a medicament (e.g., a pharmaceutical composition) containing the tdsRNA is provided. Optional other components of the medicament include excipients and a vehicle (e.g., aqueous buffer or water for injection) packaged aseptically in one or more separate containers (e.g., nasal applicator or injection vial). Further embodiments will be apparent from the disclosure and claims herein.

Administration

Administration Methods

Any compound, formulation, or pharmaceutical composition in this disclosure may be administered by any of the administration methods disclosed or any local or systemic route known in the art including enteral (e.g., oral, feeding tube, enema), topical (e.g., device such as a nebulizer for inhalation through the respiratory system, skin patch acting epicutaneously or transdermally, suppository acting in the rectum or vagina), and parenteral (e.g., subcutaneous, intravenous, intramuscular, intradermal, or intraperitoneal injection, buccal, sublingual, or transmucosal, inhalation or instillation intranasally or intratracheally).

In some embodiments, the tdsRNA is administered continuously. In some embodiments, the tdsRNA is administered intermittently.

The pharmaceutical composition and/or the active agents including tdsRNA for administration may be micronized by milling or grinding solid material, dissolved in a vehicle (e.g., sterile buffered saline or water) for injection or instillation (e.g., spray), topically applied, or encapsulated in a liposome or other carrier for targeted delivery. The preferred administration route may vary with the age, condition, gender, or health status of the subject, the nature of the disease or other pathological condition, including the number and severity of symptoms, and the chosen active ingredient.

Suitable effective treatment protocols include, for example, administering to a subject a therapeutically or prophylactically effective amount of a tdsRNA, preferably via at least one local or systemic route and/or by using at least one mode of administration or device as described above.

In some embodiments, a combination treatment of the present disclosure comprises administration of tdsRNA and one or more antiviral agents (e.g., interferon, cyclophilin inhibitor such as cyclosporine A, nucleoside analog such as ribavirin, protease inhibitor such as lopinavir or ritonavir, antibody specific for the Wuhan coronavirus) to an infected subject. The combination treatment may be administered in any suitable manner known in the art. For example, the tdsRNA may be administered sequentially (at different times) or concurrently (at the same time) with the one or more antiviral agents. Also, tdsRNA and one or more antiviral agents (separately or together) may be administered prophylactically (i.e., before infection) or at early-onset (i.e., soon after infection).

Nasal Administration

While this section refers to tdsRNA as an example, the administration methods described below and in this disclosure are understood to be equally applicable to any compound of this disclosure. Nonlimiting examples of these compounds include tdsRNA, RNA, DNA, adjuvants, proteins, interferons, pathogens (intact, inactivated, attenuated) or parts thereof. Nonlimiting examples of pathogens include at least viruses, bacteria, yeast, fungi and the like. "Parts thereof" of a pathogen would include at least unpurified antigens from a pathogen such as unpurified protein from a pathogen which may also include unpurified proteins from culture material or host cells. "Parts thereof" of a pathogen may also be semi-purified, purified protein from a preparation of pathogens, or recombinant proteins. Preferred embodiments of compounds for administration include tdsRNA, influenza virus including inactivated or attenuated forms and antigens thereof, coronavirus including inactivated or attenuated forms and antigens thereof. We note that tdsRNA is stable as a solid or dissolved in water and therefore any additional component is optional. Other components may benefit from additional ingredients described herein.

The tdsRNA is preferably administered to the lung(s) or nasal passage of a subject by any suitable means. tdsRNA may be administered by administering an aerosol suspension of respirable solid or liquid particles containing tdsRNA which the subject inhales. The tdsRNA can be aerosolized in a variety of forms, such as, but not limited to, dry powder inhalants, metered-dose inhalants, or liquid/liquid suspensions. The respirable particles may be liquid or solid. The particles may optionally contain other therapeutic ingredients. In reference to nasal/lung administration, the term "particle" can refer to solid or liquid particles.

The particulate pharmaceutical composition may optionally be combined with a carrier to aid in dispersion or transport. A suitable carrier such as a sugar (i.e., dextrose, lactose, sucrose, trehalose, mannitol) may be blended with the tdsRNA in any suitable ratio (e.g., a 1 to 1 ratio by weight).

In one embodiment, nasal administration of tdsRNA includes administration by inhalation. Administration by "inhalation" generally refers to the inspiration of liquid or solid particles comprised of tdsRNA that are of respirable size, that is, particles of a size sufficiently small to pass through the mouth or nose and larynx, past the oropharyngeal region, upon inhalation and into the bronchi and alveoli of the lungs. In general, particles ranging from about 1 to 10 microns in size (more particularly, less than about 5 microns in size) are respirable and suitable for administration by inhalation.

In another embodiment, a tdsRNA is topically delivered by intranasal administration. As used in this specification, "intranasal" administration refers to administration of a dosage form formulated and delivered to topically treat the nasal epithelium. Particles or droplets used for intranasal administration generally have a diameter that is larger than those used for administration by inhalation. For intranasal administration, a particle size in the range of 10-500 microns is preferred.

Liquid pharmaceutical compositions of tdsRNA for producing an aerosol can be prepared by combining the tdsRNA with a suitable vehicle, such as sterile pyrogen-free water. In certain embodiments, hypertonic saline solutions are used to carry out the present disclosure. These are preferably sterile, pyrogen-free solutions, comprising from one to fifteen percent (by weight) of a physiologically acceptable salt, and more preferably from three to seven percent by weight of the physiologically acceptable salt.

Aerosols of liquid particles comprising the tdsRNA may be produced by any suitable means, such as with a pressure-driven jet nebulizer or an ultrasonic nebulizer. Nebulizers are commercially available devices that transform solutions or suspensions of the tdsRNA into a therapeutic aerosol mist either by means of acceleration of compressed gas, typically air or oxygen, through a narrow venturi orifice or by means of ultrasonic agitation.

Suitable formulations for use in nebulizers consist of the tdsRNA optionally in a liquid carrier, the tdsRNA comprising up to 40% w/w of the formulation, but preferably less than 20% w/w. The carrier is typically water (and most preferably sterile, pyrogen-free water) or a dilute aqueous-alcoholic solution, preferably made isotonic, but may be hypertonic with body fluids by the addition of, for example, sodium chloride. Optional additives include buffers and preservatives if the formulation is not made sterile, for example, methyl hydroxybenzoate, antioxidants, flavoring agents, volatile oils, buffering agents and surfactants.

Aerosols of solid particles comprising the tdsRNA may likewise be produced with any solid particulate therapeutic aerosol generator. Aerosol generators for administering solid particulate therapeutics to a subject produce particles which are respirable and generate a volume of aerosol containing a predetermined metered dose of a therapeutic at a rate suitable for human administration. One illustrative type of solid particulate aerosol generator is an insufflator. Suitable formulations for administration by insufflation include finely comminuted powders which may be delivered by means of an insufflator or taken into the nasal cavity in the manner of a snuff. In the insufflator, the powder (e.g., a metered-dose thereof effective to carry out the treatments described herein) is contained in capsules or cartridges, typically made of gelatin or plastic, which are either pierced or opened in situ and the powder delivered by air drawn through the device upon inhalation or by means of a manually-operated pump. The powder employed in the insufflator consists either solely of the tdsRNA or of a powder blend comprising the tdsRNA, a suitable powder diluent, such as lactose, and an optional surfactant. The tdsRNA typically comprises from 0.1% to 100% w/w of the formulation.

Another type of illustrative aerosol generator comprises a metered-dose inhaler. Metered-dose inhalers are pressurized aerosol dispensers, typically containing a suspension or solution formulation of the tdsRNA in a liquefied propellant. During use these devices discharge the formulation through a valve adapted to deliver a metered volume, typically from 10 μl to 200 μl, to produce a fine particle spray containing the tdsRNA. Suitable propellants include certain chlorofluorocarbon compounds, for example, dichlorodifluoromethane, trichlorofluoromethane, dichlorotetrafluoroethane and mixtures thereof. The formulation may additionally contain one or more co-solvents, for example, ethanol, surfactants, such as oleic acid or sorbitan trioleate, antioxidant and suitable flavoring agents.

The preferred route and mode of administration will vary with the condition and age of the recipient, the nature of the infection or condition, and the chosen active ingredient.

Subject

As used herein, a "subject" has the same meaning as a "patient" and is a mammal, preferably, a human or another host animal for a virus listed in this disclosure. In addition to humans, categories of mammals within the scope of the present disclosure include, for example, farm animals, domestic animals, laboratory animals, etc. Some examples of farm animals include cows, pigs, horses, goats, etc. Some examples of domestic animals include dogs, cats, etc. Some examples of laboratory animals include primates, rats, mice, rabbits, guinea pigs, etc. Other examples of subjects include any animal that may harbor coronaviruses such as civet cats, swine, cattle, horses, camels, cats, dogs, rodents, birds, bats, rabbits, ferrets, mink, snake, and the like. As used herein, the terms "patient" or "subject" are used interchangeably.

Dosage

For a subject (e.g., 150 lb. or 70 Kg human) the dose of dsRNA may range from 0.1 to 1,000,000 μg, preferably from 0.4 to 400,000 μg. If desired, the dosage may be scaled to other subjects of a different mass. For example, tdsRNA may be dosed at from about 0.5 mg to about 60 mg per day,
from about 5 mg to about 400 mg per day,
from about 25 mg to about 700 mg per day,
or from about 10 mg to about 800 mg per day in a subject.

As another example, the administration may be in 50-1400 milligrams every other day leading to an average daily dosage of 25-700 milligrams per day.

In certain embodiments, the tdsRNA is administered in a dose of 0.1 mg/kg, 0.2 mg/kg, 0.3 mg/kg, 0.5 mg/kg, 0.7 mg/kg, 0.8 mg/kg, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 15 mg/kg or 20 mg/kg.

In another embodiment, the dosage of a tdsRNA of the present disclosure is a unit dose of about 0.1-20 mg/kg, about 0.1-10 mg/kg, about 0.1-8 mg/kg, about 0.1-7 mg/kg, about 0.1-6 mg/kg, about 0.1-5 mg/kg, about 0.1-4 mg/kg, about 0.1-3 mg/kg, about 0.2-3 mg/kg, about 0.3-3 mg/kg, about 0.4-3 mg/kg, about 0.6-3 mg/kg, about 0.8-3 mg/kg, about 0.1-2 mg/kg, about 0.1-1 mg/kg.

Total daily dose may vary from 20 mg to 200 mg 50 mg to 150 mg, 80 mg to 140 mg.

In a preferred embodiment, a tdsRNA is administered at a unit dose of about 0.1 mg/kg, about 0.2 mg/kg, about 0.4 mg/kg, about 0.6 mg/kg, about 0.8 mg/kg, about 1 mg/kg, about 2 mg/kg, about 3 mg/kg, about 4 mg/kg or about 5 mg/kg.

In one embodiment, the tdsRNA is administered at a dose from about 1 mg/kg to 10 mg/kg biweekly.

In certain embodiments, the tdsRNA is administered one dose per day, one dose every 2 days, one dose every 3 days, one dose every 4 days, one dose every 5 days, once a week, once every two weeks, or once every four weeks, preferably one dose every 3 days.

In certain embodiments, the tdsRNA is administered as a single dose, in two doses, in three doses, in four doses, in five doses, or in 6 or more doses.

The dosing schedule can vary from, e.g., once a week to once every 2 weeks, once a week to once every 3 weeks, once a week to once every 4 weeks. In one embodiment, the tdsRNA is administered at a dose from about 0.50 mg/kg to 10 mg/kg every other week. In certain embodiments, the dose frequency may vary from once a day to once a month.

The recommended dosage of tdsRNA will depend on the clinical status of the subject and the physician's or veterinarian's experience treating the disease or other pathological condition. tdsRNA may be dosed at from about 0.5 mg to about 60 mg per day, from about 5 mg to about 400 mg per day, from 25 mg to about 700 mg per day, or from about 10 mg to about 800 mg per day in a subject (e.g., body mass of about 70 80 Kg for a human patient) on a schedule of either once a day up to 7 days weekly or once-weekly to thrice-weekly (preferably twice weekly), albeit the dose amount and/or frequency may be varied by the physician or veterinarian in response to the subject's symptoms. That is, for example, the administration may be in 50-1400 milligrams every other day leading to an average daily dosage of 25-700 milligrams per day.

A dosing period is usually about 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 days, and, in one embodiment, 6, 7, 8, 9, 10, 11, 12, 13, or 14 days, for example, 7 or 14 days.

In certain embodiments, multiple (for example, 2, 3, 4, 5, 6, 7, 8, 9, 10 or more) doses of a tdsRNA are administered to a subject in need of treatment.

Analysis

Analysis of the base composition of RNA whether single-stranded or double-stranded may be performed by one of ordinary skill in the art. For example, the molar ratio of Cytidine to Uridine (C:U) in Poly $C_{12}U$ can be determined by hydrolysis of the polymer to its constituent nucleotides. The nucleotides are separated by High Performance Liquid Chromatography and quantitated by ultraviolet absorption. The polymers were hydrolyzed by RNase. An example of a solvent system, which can be used for the gradient chromatography is 100 mM Triethylammonium acetate, pH 6.0 and Acetonitrile.

Viruses that can be Treated tdsRNA, alone or in combination with other active ingredients, can be used to prevent and/or treat infection by one or more viruses. Treatment encompasses reducing or shortening the duration of at least one symptom of a viral infection, preventing transmission of a virus, reducing a titer such as a nasal titer of a virus, and preventing infection. The other active ingredients may be vaccines. Vaccines may comprise viral antigens, whole viruses (e.g., a less virulent strain), attenuated viruses, inactivated viruses, and the like. The viruses that can be treated by tdsRNA and the methods of this disclosure may any virus, and these viruses may include at least the ones listed below or anywhere in this disclosure.

Influenza

Influenza viruses belong to the Orthomyxoviridae family of viruses, which includes five genera: Influenzavirus A, Influenzavirus B, Influenzavirus C, Isavirus, and Thogotovirus. Dhori virus is a species of the genus Thogotovirus. An influenza virus can infect humans and other species. Influenza type A viruses can infect humans, birds, pigs, horses, seals and other animals. Wild birds can be natural hosts for these viruses.

Influenza Type A

Influenza type A viruses can be divided into subtypes and named on the basis of two proteins on the surface of the virus: hemagglutinin (HA) and neuraminidase (NA). For example, an "H7N2 virus" designates an influenza A subtype that has an HA7 protein and an NA2 protein. Similarly, an "H5N1" virus has an HA 5 protein and an NA 1 protein. There are 16 known HA subtypes and 9 known NA subtypes. Many different combinations of HA and NA proteins are possible. Any number of the known HA subtypes (HAL HA2, HA3, HA4, HAS, HA6, HA7, HA8, HA9, HA10, HA11, HA12, HA13, HA14, HA15, and HA16) can be combined with any number of the known NA subtypes (NA1, NA2, NA3, NA4, NAS, NA6, NA7, NAB, and NA9) to produce a vaccine to prevent or treat an infection. The HA and NA subtypes can also be used individually in a vaccine to prevent infection. Different subtype vaccines can be combined at the point of use, either sequentially or simultaneously, to prevent an infection. Some influenza A subtypes (e.g., H1N1, H1N2, and H3N2) are currently in general circulation among people. Other subtypes can be found in other animal species. For example, H7N7 and H3N8 viruses can cause illness in horses, and H3N8 also has recently been shown to cause illness in dogs.

Influenza Type B

Influenza B viruses can be found in humans and can also infect seals. Unlike influenza A viruses, these viruses are not classified according to subtype. Influenza B viruses can cause morbidity and mortality among humans, but in general are associated with less severe epidemics than influenza A viruses. Although influenza type B viruses can cause human epidemics, they have not caused pandemics.

Influenza Type C

Influenza type C viruses can cause mild illness in humans and do not cause epidemics or pandemics. These viruses can also infect dogs and pigs. These viruses are not classified according to subtype.

Coronavirus

Coronavirus has emerged as a new threat to human health and safety. Known coronaviruses such as strains 229E, NL63, OC43, and HKU1 result in only mild respiratory infections in healthy adults. However, strains such as SARS-CoV, MERS-CoV, and SARS-CoV-2 are significantly more lethal.

Other Viruses

The methods and compositions described herein can be useful for the prevention and/or treatment of infection by any virus, including, for example, the viruses listed below:

Adeno associated virus group, herpes simplex virus 2,
Adenovirus, herpesvirus,
Burkitt's lymphoma virus, herpesvirus 7,
Coronavirus, human adenovirus
Cytomegalovirus, human immunodeficiency virus,
EB virus, human immunodeficiency virus 1,
Ebola virus, human immunodeficiency virus 2,
EIA virus, human papillomavirus,
encephalitis virus, human T cell leukemia virus,
German measles virus, human T cell leukemia virus I,
Hantavirus, human T cell leukemia virus II,
hemorrhagic fever virus, human T cell leukemia virus III,
hepatitis A virus, human T cell lymphoma virus I,
hepatitis B virus, human T cell lymphoma virus II,
hepatitis C virus, human T cell lymphotropic virus type 1,
hepatitis D virus, human T cell lymphotropic virus type 2,
hepatitis delta virus, human T lymphotropic virus I,
hepatitis E virus, human T lymphotropic virus II,
hepatitis F virus, human T lymphotropic virus III,
hepatitis G virus, influenza virus A,
hepatitis nonA nonB virus, influenza virus B,
hepatitis virus, influenza virus C,
herpes B virus, influenza virus D,
herpes simplex virus, influenza virus pr8,
herpes simplex virus 1, measles virus,
mumps virus, parainfluenza virus type 3,
parainfluenza virus, parainfluenza virus type 4,
parainfluenza virus type 1, West Nile virus,
parainfluenza virus type 2, Other Aspects In this specification, stating a numerical range, it should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity that a person skilled in the art would understand does not affect the operation of the invention or its patentability.

All modifications and substitutions that come within the meaning of the claims and the range of their legal equivalents are to be embraced within their scope. A claim which recites "comprising" allows the inclusion of other elements to be within the scope of the claim. The invention is also described by such claims reciting the transitional phrases "consisting essentially of" (i.e., allowing the inclusion of other elements to be within the scope of the claim if they do not materially affect the operation of the invention) or "consisting of" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrangement of components in a product claim or order of steps in a method claim is not a limitation of the claim unless explicitly stated to be so). All possible combinations and permutations of individual elements disclosed herein are considered to be embodiments of the invention. Similarly, generalizations of the invention's description are considered to be part of the invention.

From the foregoing, it would be apparent to a person of skill in this art that the invention can be embodied in other specific forms without departing from its spirit or essential characteristics.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

INCORPORATION BY REFERENCE

All publications, patent applications, and patents mentioned herein are hereby incorporated by reference in their entirety as if each individual publication or patent was specifically and individually indicated to be incorporated by reference. These patents include, at least, U.S. Pat. Nos. 4,024,222, 4,130,641, 5,258,369, 7,439,349, 8,722,874 and 9,315,538. In case of conflict, the present application, including any definitions herein, will control.

EXAMPLES

Example 1 tdsRNA Synthesis and Purification

Strand synthesis was performed by polymerization of ribonucleotide diphosphates using polynucleotide phosphorylase (PNPase) made from M. *Luteus* bacteria. PNPase catalyzes both processive 3'→5' phosphorolysis and 5'→3' polymerization of RNA. Unlike RNA polymerases, PNPase neither requires a template nor can transcribe one. When a mixture of ribonucleotide diphosphates (NDPs) serves as the substrate for the polymerization reaction, the ensuing polymerization reaction forms a random copolymer. Conversely, when only one type of ribonucleotide diphosphate was present as the substrate for the polymerization reaction, the product will be a polymer of a single type of subunit.

Synthesis of the first ssRNA (referred to herein as the first synthesis reaction) was performed in purified water and with PNPase with the following ingredients: ribonucleotide diphosphate 22 mM; Tris(hydroxymethyl)aminomethane 100 mM; $MgCl_2$ 5 mM; EDTA 1 mM; Urea 300 mM.

Where ssRNA with the structure of $rI_n$ was desired, the ribonucleotide diphosphate poly(I) at the prescribed concentration of 22 mM was the only ribonucleotide diphosphate present in the reaction.

Synthesis of the second ssRNA (referred to herein as the second synthesis reaction) was performed as follows. In the case where ssRNA comprising C and U subunits was desired, the reaction was performed in purified water and with PNPase with the following ingredients: ribonucleotide diphosphates 22 mM total—comprising a mixture of rCDP and rUDP, where a ratio of (molar concentration of rCDP):(molar concentration of rUDP) was 12; Tris(hydroxymethyl)aminomethane 100 mM; $MgCl_2$ 5 mM; EDTA 1 mM; Urea 300 mM.

Where a ssRNA with the structure of $r(C_{12}U)_n$ for example was desired, the ribonucleotide diphosphates rCDP and rUDP at a molar ratio of rCDP:rUDP=12 and a total concentration of 22 mM are the only ribonucleotide diphosphate present in the reaction.

The first synthesis reaction and the second synthesis reaction were performed in separate reactions and in separate vessels. Naturally, the first synthesis reaction and the second synthesis reaction can be performed in any order. Reaction was started by the addition of PNPase as the sole RNA polymerase in the range of 500-700 Units per Liter of reaction. The reaction temperature was maintained at 21° C.-25° C. for 12 to 48 hours. All of the synthesis reactions were performed in the absence of any ATP, in the absence of DNA components (i.e., DNA, DNA templates, dNTPs, dNDPs, dNMPs), and in the absence of any ribo bases that are not desired to be incorporated into the ssRNA chain.

For example, if the first synthesis reaction was designed to synthesize $rI_n$, then the synthesis reaction was performed in the absence of rATP, rADP, rAMP, rUTP, rUDP, rUMP, rGTP, rGDP, rGMP, rCTP, rCDP, rCMP, rITP, and rIMP. That was because only rIDP was needed, rIDP was the only nucleotide in the reaction.

As another example, if the second synthesis reaction was designed to synthesize $r(C_{12}U)_n$, then the synthesis reaction was performed in the absence of rATP, rADP, rAMP, rUTP, rUMP, rGTP, rGDP, rGMP, rCTP, rCMP, rITP, rIDP and rIMP. That was because only rCDP and rUDP was needed.

RNA chain elongation was stopped by adding $EDTA-Na_2$ until $EDTA-Na_2$ concentration reached 26.9 mM.

Synthesized ssRNA from the first or the second synthesis reaction were purified as follows. Purification comprises four phenol extractions in the presence of SDS and Tris. The "phenol" used in phenol extraction was a composition of phenol: chloroform: isoamyl alcohol (25:24:1) at a pH of between 4-6. As a substitute, acid guanidinium thiocyanate-phenol-chloroform extraction may be used instead of phenol extraction. After each phenol extraction, the aqueous layer was collected and after the final extraction, the aqueous solution was precipitated in alcohol at a KCl concentration of 450 mM—achieved by the addition of KCl. The resulting precipitate was dissolved in water, and precipitated again in alcohol with 450 mM KCl. The precipitate was dissolved in water forming a solution of ssRNA. 10 mM $EDTA-K_2$ was added to substitute the $K^+$ ions for the $Na^+$ ions. $EDTA-K_2$ prevents the degradation of RNA and functions as an RNase inhibitor. This solution was concentrated and dialyzed against 7 volumes of water with 10 mM $KC_2H_3O_2$ to remove the salts and ribonucleotide diphosphates, thus producing an aqueous solution containing single-stranded RNA. This solution was filtered through a 0.22 um filter.

The aqueous single-stranded RNA solutions are brought to a final concentration of 7.9 mM in sodium phosphate buffer (150 mM NaCl; 1 mM $MgCl_2$; 8 mM $Na_2HPO_4$; 1.6 mM $NaH_2PO_4$). Equivalent volumes of the two single-stranded RNA solutions, at equivalent molar concentrations of first single-stranded RNA and second single-stranded RNA were mixed by slow addition of one solution to a second solution with stirring for at least 5 minutes. The mixed solution was heated to 65° C. for up to 30 minutes and then to 50° C. over 30 minutes.

The solution was then filtered by a 0.22 micron sterile filter to produce tdsRNA (a dsRNA). Products of the most desirable quality were produced when the above protocol was performed sequentially without interruption or intermediate storage steps such as lyophilization, drying, resuspension etc. between steps to minimize any changes to the dsRNA.

The above process has been repeated multiple times with consistent results and produces a tdsRNA which is further described in this disclosure. Rintatolimod in all the examples of this disclosure refers to rintatolimod made using the process of this example. Further, while the above disclosed method has been disclosed for one formula or some formulas of tdsRNA, all the formulas of tdsRNA may be made using this disclosed method.

Example 2 Culturing SARS-CoV-2 and Host Cells

Methods for culturing SARS-CoV-2 are published in Journals. See, e.g., Harcourt et al., Emerging Infectious Diseases, Vol. 26, No. 6, June 2020, pages 1266-1273.

Human airway epithelial cell culture has been known for over 20 years (see, e.g., Lechner, J. F., Haugen, A., McLendon, I. A., and Pettis, E. W. (1982) Clonal growth of normal adult human bronchial epithelial cells in a serum-free medium. In Vitro 18, 633-642). Human airway epithelial cells are harvested directly from humans according to established protocols (Jonsdottir H R, Dijkman R. Coronaviruses and the human airway: a universal system for virus-host interaction studies. Virol J 2016; 13:24-24). Human airway epithelial cell cultures maintained at an air-liquid interface (ALI) is known and well described (Fulcher, M. L., Gabriel, S.; Burns, K. A., Yankaskas, J. R., Randell, S. H., Well-Differentiated Human Airway Epithelial Cell Culture, in Methods in Molecular Medicine, Vol. 107: Human cell Culture Protocols, Second Edition, Edited by: J. Picot, Humana Press Inc. Totowa, NJ). Primary cells such as "Normal Human Bronchial Epithelial Cells-P1" (catalog number: NhBE-P1) are also available commercially for example, by Novabiosis (North Carolina, U.S.A.). These cells are suitable for growing SARS-CoV-2 cells in vitro (Zhu, N., et al, "A Novel Coronavirus from Patients with Pneumonia in China, 2019"; published on the web from the New England Journal of Medicine Jan. 24, 2020).

Bronchoalveolar-lavage fluid are collect from infected subjects and the collected samples are centrifuged to remove cellular debris. The supernatants containing coronavirus (e.g., SARS-CoV-2) are propagated on human airway epithelial cells as described herein.

To prepare cells for virus propagation, human airway epithelial cells are expanded on plastic substrate to generate passage-1 cells and are subsequently plated at a density of $2.5 \times 10^5$ cells per well on permeable Transwell-COL (12-mm diameter) supports. Human airway epithelial cell cultures are generated in an air-liquid interface for 4 to 6 weeks to form well-differentiated, polarized cultures resembling in vivo pseudostratified mucociliary epithelium.

Prior to infection, the apical surfaces of the human airway epithelial cells are washed three times with phosphate-buffered saline. Infection is initiated by adding 150 µl of supernatant from bronchoalveolar-lavage fluid samples (as described above) or from a previous SARS-CoV-2 preparation onto the apical surface of the cell cultures. After a 2-hour incubation at 37° C., unbound virus is removed by washing with 500 µl of phosphate-buffered saline for 10 minutes. The human airway epithelial cells are maintained in an air-liquid interface incubated at 37° C. with 5% carbon dioxide. Every 48 hours, 150 µl of phosphate-buffered saline is applied to the apical surfaces of the human airway epithelial cells, and after 10 minutes of incubation at 37° C. the samples are harvested as new SARS-CoV-2 virus harvests. The viral title is monitored by RT-PCR and by infecting new cultures and observing cytopathic effects (CPE).

Example 3: Example of Growing Host Cells Susceptible to SARS-CoV-2, Infecting the Cells with SARS-CoV-2, and Testing Rintatolimod To test the efficacy of rintatolimod made by the methods of this disclosure, experiments were performed an in vitro study to determine the antiviral efficacy of rintatolimod against severe acute respiratory syndrome coronavirus 2 (SARS-CoV-2) in human-derived tracheal/bronchial epithelial cells. All rintatolimod in this Example were made by us following the procedures and methods of this disclosure.

The antiviral activity of AIM ImmunoTech's compound rintatolimod was evaluated against SARS-CoV-2 (strain USA-WA1/2020) in a highly differentiated, three-dimensional (3-D), in vitro model of normal, human-derived tracheal/bronchial epithelial (TBE) cells. The compounds were tested at 5 concentrations in triplicate inserts of the 3D tissue models of the human airway (MatTek Life Sciences) as indicated in Table 1. Antiviral activity was measured by virus yield reduction assays 5 days after infection.

Compounds: Rintatolimod was provided as 25 frozen 1 mL aliquots at 2.5 mg/mL and stored at −20° C. upon arrival. A fresh vial of the compound was diluted to the test dilutions (100, 50, 25, 12.5, and 6.25 μg/mL) in the MatTek culture medium (AIR-100-MM) just prior to each drug addition using RNase-free tubes, pipettes and pipet tips. Remdesivir (MedChemExpress, cat #HY-104077) was tested in singlet wells at 1, 0.1, 0.01, and 0.001 μg/mL as the positive control.

Cell Culture: The EpiAirway™ Model consists of normal, human-derived tracheal/bronchial epithelial (TBE) cells which have been cultured to form a multi layered, highly differentiated model which closely resembles the epithelial tissue of the respiratory tract. The cell cultures were made to order by MatTek Life Sciences (https://www.mattek.com) (Ashland, MA) and arrived in kits with either 12- or 24-well inserts each. The TBE cells were grown on 6 mm mesh disks in transwell inserts. During transportation the tissues were stabilized on a sheet of agarose, which was removed upon receipt. One insert was estimated to consist of approximately $1.2\times10^6$ cells. Kits of cell inserts (EpiAirway™ AIR-100) originated from a single donor, #9831, a 23-year old, healthy, non-smoking, Caucasian male. The cells have unique properties in forming layers, the apical side of which is exposed only to air and that creates a mucin layer. Upon arrival, the cell transwell inserts were immediately transferred to individual wells of a 6-well plate according to manufacturer's instructions, and 1 mL of MatTek's proprietary culture medium (AIR-100-MM) was added to the basolateral side, whereas the apical side was exposed to a humidified 5% $CO_2$ environment. The TBE cells were cultured at 37° C. for 5 h.

Viruses: SARS-CoV-2 strain USA-WA1/2020 was passaged three times in Vero 76 cells to create the virus stock. Virus was diluted in AIR-100-MM medium before infection, yielding a multiplicity of infection (MOI) of approximately 0.005 $CCID_{50}$ per cell.

Experimental design: After the 5 h equilibration period, the cells were treated with drug on the basal side of the transwells and cultured at 37° C. for 18 h. The mucin layer, secreted from the apical side of the cells, was removed by washing with 400 μL pre-warmed 30 mM HEPES buffered saline solution 3×. Each compound treatment (120 μL) and virus (120 μL) was applied to the apical side, and compound treatment only was applied to the basal side (1 mL), for a 2 h incubation. As a virus control, 4 of the cell wells were treated with placebo (cell culture medium only). Following the 2 h infection, the apical medium was removed, and the basal side was replaced with fresh compound or medium. The cells were maintained at the air-liquid interface. The basal side compound was replaced again at 6 h, 36 h, 48 h, and 72 h after the infection. On day 5, the medium was removed and discarded from the basal side. Virus released into the apical compartment of the tissues was harvested by the addition of 400 μL of culture medium that was pre-warmed at 37° C. The contents were incubated for 30 min, mixed well, collected, thoroughly vortexed and plated on Vero 76 cells for VYR titration. Triplicate and singlet wells were used for virus control and cell controls, respectively.

Determination of virus titers from each treated cell culture: Vero 76 cells were seeded in 96-well plates and grown overnight (37° C.) to 90% confluence. Samples containing virus were diluted in 10-fold increments in infection medium and 200 μL of each dilution transferred into respective wells of a 96-well microtiter plate. Four microwells were used for each dilution to determine 50% viral endpoints. After 5 days of incubation, each well was scored positive for virus if any cytopathic effect (CPE) was observed as compared with the uninfected control, and counts were confirmed for endpoint on day 7. The virus dose that was able to infect 50% of the cell cultures (CCID50 per 0.1 mL) was calculated by the Reed-Muench method (1948). The day 5 values are reported. Untreated, uninfected cells were used as the cell controls.

MTT cytotoxicity assay: The MTT assay is used as an indicator of cell viability. The colorimetric assay is based on the reduction of a yellow tetrazolium salt to purple formazan crystals by live cells. The formazan crystals are then dissolved using a solubilization solution (10% SDS prepared in PBS) and the resulting colored solution is quantified by measuring absorbance at 550 nanometers using a multi-well spectrophotometer.

The test compound was provided as 3 frozen 6 mL aliquots at 10.3 mg/mL prepared in MatTek's proprietary culture medium (AIR-100-MM and stored at −20 □C upon arrival. A fresh vial of the compound was diluted to the test dilutions (10, 4.5, 1.5, and 0.5 mg/mL) in the MatTek culture medium just prior to each drug addition using RNase-free tubes, pipettes and pipet tips. Two tissues treated with medium only were used as the cell controls.

After the 24 h equilibration period, the mucin layer, secreted from the apical side of the cells, was removed by washing with 400 μL pre-warmed 30 mM HEPES buffered saline solution 3×. Each compound treatment (240 μL) was applied to the apical side and to the basal side (1 mL), for a 2 h incubation at 37° C. As a cell control, 2 cell wells were treated with placebo (cell culture medium only). Following the 2 h incubation (to mimic the conditions of a virus infection), the apical medium was removed, and the cells were maintained at the air-liquid interface. The basal side compound was replaced again at 48 and 96 h after the mock infection. On day 5, the apical side was washed 1× with PBS, 0.1 mL of MTT was applied to the apical side and incubated at 37° C. overnight for the cytotoxicity assay. Any remaining liquid was then removed from the apical and basal sides and 0.2 mL of solubilization solution added to the cell inserts and incubated at 37° C. overnight. The solution was then transferred to a 96-well flat-bottom plate and read by a spectrophotometer. Triplicate and singlet wells were used for virus control and cell controls, respectively.

Results

The virus yield results and $EC_{90}$ values are summarized in Table 1.

Rintatolimod tested at 10 mg/mL was 47% cytotoxic, 4.5 mg/mL was 12% cytotoxic, and the lower concentrations had no measurable toxicity. The data indicate that the cell cytotoxicity concentration of compound that would cause 50% cell death ($CC_{50}$) is >10 mg/mL in the tested tissue model of normal, human-derived tracheal/bronchial epithelial cells.

Reference: Reed, L. J., Muench, H., 1938. A simple method of estimating fifty percent endpoints. The American Journal of Hygiene 27, 493-497.

TABLE 1

Antiviral efficacy: $EC_{90}$ for AIM ImmunoTech, Inc. compound rintatolimod against SARS-CoV-2.

| Test Compounds | Concentration (µg/mL) | $^a$Log$_{10}$ CCID$_{50}$ virus per 0.2 mL | $^b$EC$_{90}$ (µg/mL) |
|---|---|---|---|
| Rintatolimod | 100 | 3.00 | 49 |
|  | 50 | 3.67 |  |
|  | 25 | 4.50 |  |
|  | 12.5 | 4.67 |  |
|  | 6.25 | 4.50 |  |
| Rintatolimod | 100 | 3.00 | 55 |
|  | 50 | 4.00 |  |
|  | 25 | 4.30 |  |
|  | 12.5 | 4.30 |  |
|  | 6.25 | 4.50 |  |
| Rintatolimod | 100 | 3.50 | 39.1 |
|  | 50 | 3.50 |  |
|  | 25 | 4.00 |  |
|  | 12.5 | 4.30 |  |
|  | 6.25 | 4.30 |  |
| Remdesivir | 1 | 3.00 | 0.01 |
|  | 0.1 | 3.00 |  |
|  | 0.01 | 3.67 |  |
|  | 0.001 | 4.30 |  |
| Virus Control |  | 5.00 |  |
|  |  | 4.00 |  |
|  |  | 4.67 |  |
|  |  | 5.00 |  |

Each well was scored positive for virus if any CPE was observed as compared with the uninfected control. Vero 76 cells were scored on day 5 and confirmed on day 7.
$^a$Titer results from the virus yield reduction (VYR) assay.
$^b$EC$_{90}$ = 90% effective concentration (concentration to reduce virus yield by 1 log$_{10}$) determined by regression analysis.

Our results indicate that the SARS-CoV-2 virus count can be reduced by one order of magnitude, to 10 fold less, when tdsRNA is applied at a concentration of 55 µg/mL. To confirm that this is a safe dosage for application to humans in a clinical setting, this concentration was compared to clinically achievable concentration based on the intranasal safety profile of rintatolimod as shown below.

TABLE 2

The $EC_{90}$ of Rintatolimod Against SARS-CoV-2 in a 3-D In Vitro Model of Normal, Human-derived Tracheal/Bronchial Epithelial Cells was 39.1-55 µg/ml, a Clinically Achievable Concentration Based on the Intranaal Safety Profile of Rintatolimod.

| Intranasal Rintatolimod dose (µg) | Dose Volume[1] (µl) | Dose Concentration (µg/ml) | Rintatolimod $EC_{90}$[2] (µg/ml) | Fold Dose Conc. Increase Over $EC_{90}$ |
|---|---|---|---|---|
| 200 | 500 | 400 | 55 | 7.3 |
| 500 | 500 | 1000 | 55 | 18.2 |
| 1250 | 500 | 2500 | 55 | 45.5 |

[1]Dose volume is split equally between each nostril.
[2]Highest EC90 value obtained.
[3]For the well tolerated dose concentration of 2500 µg/ml, it represents a 45.5 fold increase relative to the EC90 at 55 µg/ml.

As can be seen, rintatolimod made by the methods of this disclosure has high antiviral activity against SARS-CoV-2 as shown by $EC_{90}$ at rintatolimod concentrations that are well tolerated in humans. In fact, as shown in Table 2 above, a dosage that is 45 fold higher (i.e., 45×$EC_{90}$ dose) is well tolerated in humans. Thus, tdsRNA and especially tdsRNA made by the process of this disclosure is effective and well tolerated for the treatment or prevention of SARS-CoV-2 infection or for the reduction of SARS-CoV-2 titer on nasal tissue.

Rintatolimod has been tested in vitro in a SARS-CoV-2 infection model in human-derived tracheal/bronchial epithelial cells. Rintatolimod decreased SARS-CoV-2 infectious viral yields by 90% (EC90) at clinically achievable intranasal dosage levels (Table 1). In the same human-derived tracheal/bronchial epithelial cell system, the cell cytotoxicity 50% (CC50) of Rintatolimod was >10 mg/mL. Rintatolimod concentrations of 1.5 mg/ml and 0.5 mg/ml induced no cellular toxicity (0%).

As a further test of the ability of tdsRNA to enhance protection against SARS-CoV-2, the following in vivo experiments were performed as follows:

"0 day" and "0 Week" is defined as the day and week of SARS-CoV-2 infection. Therefore, −1 week refers to 1 week before infection or −7 days before infection, 10 days refers to 10 days after infection. Blood sampling was performed throughout the period of experiments.

Mice were immunized at −35 days and −21 days. The dosage of SARS-CoV-2 S protein ectodomain (referred to in this Example only as S protein) is at 100 ng per mouse when administered. The dosage of tdsRNA, in the form of rintatolimod $(rI_n \cdot r(C_{12}U)_n)$, was at 10 µg per mouse when administered. All immunizations were performed by subcutaneous injection.

Group 1 mice were administered S protein only. Group 2 mice were administered S protein and tdsRNA. Group 3 mice were sham administered phosphate buffered saline. As discussed, infection was at 0 day.

Neutralization antibody in the serum was measured at −7 days which is 2 weeks after the second immunization but before infection. Group 3 mice (sham immunized) has a relative titer of 2 (log$_2$) representing a baseline of the measuring methods. Group 1 mice (S protein only) has a relative titer of 4 (log$_2$). Group 2 mice (S protein and tdsRNA) has a relative titer of 16 (log$_2$).

Viral titers after infection were measured. Group 3 mice (sham immunized) has a viral titer (Log 10/g) of 8.7. Group 1 mice (S protein only) has a viral titer (Log 10/g) of 8. Group 2 mice (S protein and tdsRNA) have a viral titer (Log 10/g) of 6, ⅒ of the Group 1 mice because the scale is Log$_{10}$/g.

Group 3 mice (sham immunized) lost weight linearly until they reached 70% of their initial weight 5 days after infection at which point they died from the infection. Group 1 mice (S protein only) had a weight reduction to 83% by day 3 and about 95% by day 10. Group 2 mice (S protein and tdsRNA) had a weight reduction to 87% by day 3 and gained weight by day 10 to reach a level of 105%. All weight percent were measured as a percentage of initial weight at the moment of infection which was set as 100%.

Survival data were most dramatic. Group 3 mice (sham immunized) ⅓ of the mice died at day 5 and all mice died by day 6. Group 1 mice (S protein only) had ⅙ death by day 6 and survival was ⅚ by day 10. In contrast, Group 2 mice (S protein and tdsRNA) had 100% survival by day 10.

We claim:

1. A method for synthesis of a therapeutic double-stranded RNA (tdsRNA), comprising:
   a) synthesizing a first single-stranded RNA (first ssRNA) in a first synthesis reaction with PNPase as the only RNA polymerase;
   b) synthesizing a second single-stranded RNA (second ssRNA) in a second synthesis reaction with PNPase as the only RNA polymerase; and
   c) hybridizing the first ssRNA with the second ssRNA to form the tdsRNA;
   wherein step a) and step b) are performed in any order,
   wherein the first synthesis reaction comprises inosine diphosphate (rIDP) as the only free ribonucleotide,
   wherein the second synthesis reaction comprises cytidine diphosphate (rCDP) and uridine diphosphate (rUDP) as the only two free ribonucleotides, and
   wherein the method is performed without lyophilization.

2. The method of claim 1, wherein the first synthesis reaction and the second synthesis reaction comprise one or more reagents selected from the group consisting of:
   tris(hydroxymethyl)aminomethane buffer;
   $MgCl_2$;
   EDTA;
   Urea; and
   PNPase.

3. The method of claim 1, wherein a molar ratio of free rCDP/free rUDP in the second synthesis reaction is about 4 to 29:1.

4. The method of claim 1, wherein the first synthesis reaction and the second synthesis reaction are performed in the absence of
   adenosine triphosphate (ATP);
   free rNMP;
   free rNTP;
   DNA;
   free dNTP;
   free dNDP; and
   free dNMP.

5. The method of claim 1, further comprising one or more steps selected from the group consisting of:
   purifying said first ssRNA after the first synthesis reaction and before the hybridizing step;
   purifying said second ssRNA after the second synthesis reaction and before the hybridizing step;
   wherein purifying comprises purifying said first ssRNA or said second ssRNA from PNPase, and free ribonucleotides.

6. The method of claim 1, wherein hybridizing is performed at 62° C. to 68° C. for 5 to 30 minutes followed by 50° C. for more than 30 minutes.

7. The method of claim 1, further comprising the step of purifying the tdsRNA by filtering with 0.2 micron filter after the hybridization step.

8. The method of claim 1, wherein the method comprises:
   a) synthesizing a first single-stranded RNA (first ssRNA) in a first synthesis reaction with PNPase as the only RNA polymerase, and purifying said first ssRNA after the first synthesis reaction;
   b) synthesizing a second single-stranded RNA (second ssRNA) in a second synthesis reaction with PNPase as the only RNA polymerase, and purifying said second ssRNA after the second synthesis reaction; and
   c) hybridizing the first ssRNA with the second ssRNA at 62° C. to 68° C. for 5 to 30 minutes and then 50° C. for more than 30 minutes to form the tdsRNA;
   wherein step a) and step b) are performed in any order;
   wherein the first synthesis reaction comprises inosine diphosphate (rIDP) as the only free ribonucleotide;
   wherein the second synthesis reaction comprises cytidine diphosphate (rCDP) and uridine diphosphate (rUDP) as the only two free ribonucleotides and a molar ratio of (free rCDP):(free rUDP) in the second synthesis reaction is about (11 to 14):(1).

* * * * *